United States Patent [19]

Cammann

[11] Patent Number: 4,804,271
[45] Date of Patent: Feb. 14, 1989

[54] PROCESS FOR THE IMPROVEMENT OF SELECTIVITY OF SPECTROMETRIC MEASUREMENTS AND AN APPARATUS FOR THE PERFORMANCE OF THE PROCESS

[76] Inventor: Karl Cammann, Amalienstrasse 89, 8000 München 40, Fed. Rep. of Germany

[21] Appl. No.: 26,548
[22] PCT Filed: Jul. 4, 1986
[86] PCT No.: PCT/EP86/00395
   § 371 Date: Feb. 27, 1987
   § 102(e) Date: Feb. 27, 1987
[87] PCT Pub. No.: WO87/00273
   PCT Pub. Date: Jan. 15, 1987
[51] Int. Cl.[4] ............................................. G01J 3/433
[52] U.S. Cl. ...................................... 356/416; 356/418; 356/419; 250/282
[58] Field of Search ............... 356/414, 416, 417, 418, 356/419, 51; 250/282

[56] References Cited

U.S. PATENT DOCUMENTS

| | | | |
|---|---|---|---|
| 2,834,246 | 5/1958 | Foskett et al. | 356/51 |
| 2,941,444 | 6/1960 | Frykmann | 356/419 |
| 3,740,144 | 6/1973 | Walker | 356/53 |
| 3,756,726 | 9/1973 | Astheimer | 356/416 |
| 3,877,818 | 4/1975 | Button et al. | 356/416 |
| 3,994,592 | 11/1976 | Lardon et al. | 356/419 |
| 4,033,699 | 7/1977 | Bayly et al. | 356/419 |
| 4,082,464 | 4/1978 | Johnson, Jr. | 356/418 |
| 4,090,792 | 5/1978 | Bunge | 356/419 |
| 4,176,916 | 12/1979 | Carpenter | 356/418 |
| 4,260,262 | 4/1981 | Webster | 356/418 |
| 4,521,687 | 6/1985 | Naito | 250/282 |

FOREIGN PATENT DOCUMENTS 1050561 12/1966 United Kingdom ............... 356/419

*Primary Examiner*—F. L. Evans
*Attorney, Agent, or Firm*—Willian Brinks Olds Hofer Gilson Lione Ltd.

[57] ABSTRACT

In spectrographic measurements, the selectivity (that is to say, the ratio of the signal from the analytical sample to the signal from the impurity) is of vital importance. If a narrow spectral band is filtered from the region of the spectrum to be examined by means of a filter arrangement or the like and supplied to a detector whose output signal is displayed, there is a substantial improvement in selectivity in that the filter apparatus is periodically displaced relative to the region of the spectrum to be examined, that the spectral band extending through the filter apparatus is periodically displaced over the range of the spectrum to be examined and that the output signal for the detector is transmitted to the display through a lock-in-amplifier whose phase-reference signal is proportional to the displacement.

10 Claims, 3 Drawing Sheets

1min / 6min

PROCESS FOR THE IMPROVEMENT OF SELECTIVITY OF SPECTROMETRIC MEASUREMENTS AND AN APPARATUS FOR THE PERFORMANCE OF THE PROCESS

The present invention concerns a process and apparatus for improving the selectivity of spectrometric measurements.

A substantial problem in the spectrometric measurements of the above-mentioned kind is that on the one hand the frequency response of known filter arrangements can only be narrowed to a minimum width, indeed both from physical and from technical grounds and, on the other hand, the energy passing through a very narrow band filter, which should subsequently be detected in a detector, is small. In addition, underlying problems with spectrometric measurements must be taken into account. In this connection, it is, in essence, not only a question of the signal influenced or caused by the test piece making a contribution to the test reading, but also of test piece-impurities making a substantial signal contribution-just the background. Finally, the measuring arrangements are also subject to difficulties, that is to say, disturbances occur between signal source and detector, which make a contribution to the test reading. It is necessary to eliminate all these disturbances as far as possible.

With optical emission spectroscopy, which is an important method of analysis for the determination of chemical elements in all possible matrixes, a plasma is nowadays used as emission source, in which the substance to be examined is stimulated by radiation. In order to obtain a particularly high resolution of the measurement, monochromatic illuminators which, because of their working principle, are voluminous and susceptible to failure as a result of temperature fluctuations and vibrations, are used in many cases today. These instruments are unsuited for field application. Moreover, the instruments are also very expensive, so that only intensive laboratory application is worthwhile (with several users). It is a question, for example, of only wanting to perform an optical spectrographic analysis for certain elements which, when necessary, were previously separated chromatographically, so that in many cases such an expensive monochromatic illuminator which, indeed, is capable of analyzing the whole spectrum, is not required. Compact smaller chromatic illuminators are however substantially less sensitive and also have a worse resolution. For clinically applied flame photometry for Li, Na, K and Ca-determination, fixed interference filters are used. However, these have a very large band width or half-width value of wave length transmission (best interference filters: 0.1 nm; monochromatic illuminator 0.01 nm). Thus a considerable proportion of the continuous light of each radiation source (flame background or plasma background), which varies the selectivity and the detection limit, arrives at the detector (photo cells or photo multipliers). The detection limit is in particular determined by the light intensity relationship between the analysis line and the background radiation. Weak line intensities, as they occur with trace analysis (environmental-trace-analysis) are then no longer filtered out from a statistically distributed background intensity.

A substantial problem with fixed wavelength instruments (also expensive monochromatic illuminators) is that, in certain circumstances, large measuring errors occur and remain unrecognized. This is always the case if a real test piece is introduced together with matrix material. These then change the background of the spectroscopic radiation source. With an estimate of this measuring error, the selectivity can be defined as follows:

$$\text{Selectivity} = \frac{\text{Signal}/\mu \text{ mol test substance}}{\text{Signal}/\mu \text{ mol impurity}}$$

at the relevant, fixed adjusted wavelength.

The selectivity of expensive monochromatic illuminators is not, as a rule, better than $10^3$, that is to say, $10^3$ times greaeer than for an impurity (for example, the clinical differentiation of Na from Li or Ca by chromatographical halogenide determination) causes a fault of 100%.

Nowadays, only selectivities under 100 and also several worse detection limits are obtainable with fixed interference filters.

The above-mentioned problems occur also with other spectrometric measurements, for example with the measurement of atomic absorption spectrums or emission spectrums (including fluorescence spectrums and Raman spectrums) or with measurements of mass spectrums. In each case, the problems is one of selectivity or disturbing background.

Starting from the above-mentioned state of the art, it is the object of the present invention to provide a process for the improvement of selectivity with which larger improvements are achievable with simpler means.

This object is achieved by periodically displacing (or inverting) the filter arrangement with regards to the region of the spectrum to be examined in such a way that the spectral band passing through the filter arrangement is periodically displaced over the region of the spectrum to be examined, and that the output signal of the detector is brought to the display over a phase-sensitive rectifier (Lock-in-Amplifier) whose phase reference signal is proportional to the displacement.

Through these surprisingly simple measures, an extremely high sensitivity is achieved, even if the filter arrangement is of low quality. A selectivity of over $10^6$ could be reached in a trial (identification of chlorine) with a commercially available interference filter. The achievable selectivity lies therefore in the range which is otherwise only achievable with expensive equipment.

Instead of a displacement of the filter transmission band, it is also possible to displace the region of the spectrum to be examined. This then is only possible with the examination in the wavelength range of light with the aid of the Doppler-shift effect, if it is a question of very narrow filter transmission bands as otherwise, the high speeds for the achievement of sufficient frequency shifts are only achievable with difficulty.

The process according to the invention can also be applied to the examination of mass spectrums in which either the spectrum is displaced (through alteration of the magnetic field or through an additional electrostatic deflection field), or there is periodic displacement of the aperture arrangement.

Preferred embodiments of the invention are defined in the subsidiary claims. Further features relevant to the invention are disclosed with reference to the following embodiments which are more clearly described with reference to the accompanying drawings, in which:

Figure 1:
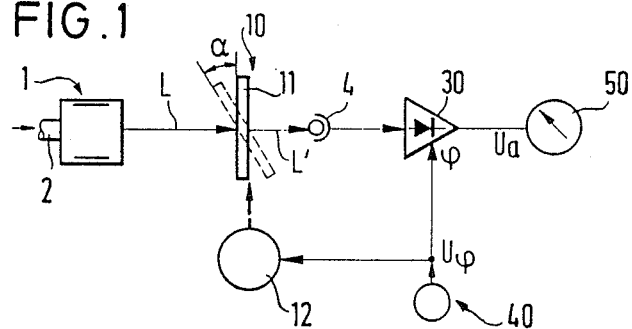
FIGS. 1 and 1a are schematic representations of an arrangement for the examination of light spectrums.
Figure 1A:
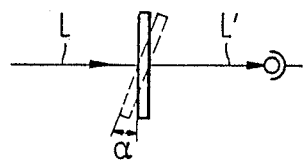

In FIG. 1., the principal testing construction for the performance of the process according to the invention, in the range of light spectroscopic examinations, is shown. The light source, a "plasma burner", which is supplied with a test gas through a connection 2, is labelled 1.

Figure 2:
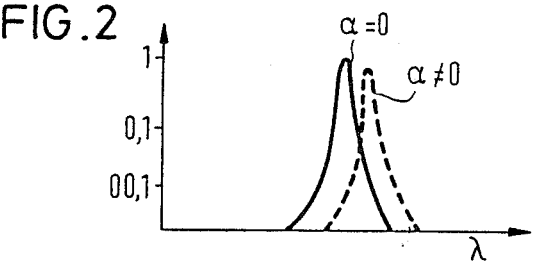
FIG. 2 is a representation of the effect resulting from the rotation of an interference filter.

The source 1 is connected in series with a suitable optical arrangement so that a substantially parallel lightbeam L can be produced, which falls on an interference filter 11. The interference filter 11 is coupled with a motor 12 in such a way that the filter 11 can be swung through an angle $\alpha$. As shown in FIG. 2, the transmission characteristic of the filter 11 is dependent on the displacement angle $\alpha$ or on the tilt angle of the filter to the lightbeam L. The light beam L' coming from the filter arrangement 10 is directed to a detector 4, for example a cooled photomultiplier. The output signal of the detector 4 is transmitted to the input of a phase-sensitive rectifier or lock-in-amplifier 30 whose output signal Ua is supplied to a measuring arrangement 50. In general, printers, display screens or the like, are used here. The phase input $\phi$ of the lock-in-amplifier 30 is connected with the output of a control generator 40 which delivers a control signal $U_\phi$. The control generator 40 can also be a component of a commercially available lock-in-amplifier 30. Furthermore, the phase signal (control signal) $U_\phi$ is supplied to the input $\phi$ of the motor 12 so that a signal is suplied to the phase input which is proportional to the swing angle $\alpha$ (or the motor itself delivers the reference signal for the lock-in-amplifier 30). On the other hand, as the position of the filter transmission characteristic is dependent on the angle $\alpha$, the amplification of the lock-in-amplifier 30 is changed in accordance with the position of the filter transmission band.

In the arrangement shown in FIG. 1, it is also possible to use a (substantially simpler and less expensive) light guide arrangement instead of a lens arrangement, if the light guide separation surface is positioned near enough to the filter 11 so that the stray light does not result in too great an effect on the broadening of the transmission characteristic.

Figure 3:
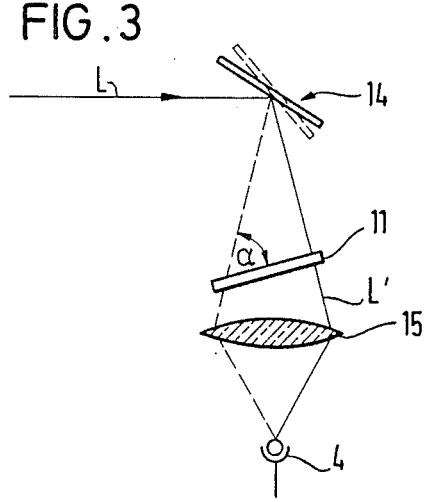
FIG. 3 shows a further preferred embodiment of the invention.

In FIG. 3, an arrangement is shown in which the filter 11 is fixed. However a mirror arrangement 14 is inserted in front of the filter 11 in the path of the light beam L. The mirror arrangement 14 is also movable by means of a motor. Because the mirror is swung, the light beam L is transmitted substantially perpendicular to the outer surface of the filter 11, in one position of the mirror, or it strikes the filter at an angle $\alpha$, in the other position of the mirror A. A convex lens 15, which focuses the filtered lightbeam L' on the detector 4 is positioned beyond the filter 11.

Both the filter 11 in the embodiment shown in FIG. 1 and the mirror 14 in the embodiment shown in FIG. 3 can be pivotally mounted over a galvanometer motor. However, a particularly preferred embodiment of the invention incorporates a torsion spring mounting for the filter or the mirror, which works in the resonance mode. Such arrangements with mirrors are commercially available as so-called "fixed frequency resonance scanners" and make oscillation frequencies of more than 10 kHz possible. Advantageously, the filter or the mirror in such an arrangement is held in a vacuum so that the damping properties of air are avoided.

With a further embodiment of the invention, not shown here, several mirrors are distributed around the periphery of a rotating drum. In this case, also, the reflected light beam is directed onto a fixed filter, so that it makes a saw-tooth trace on the filter in response to saw-tooth variation of the angle.

Figure 4:
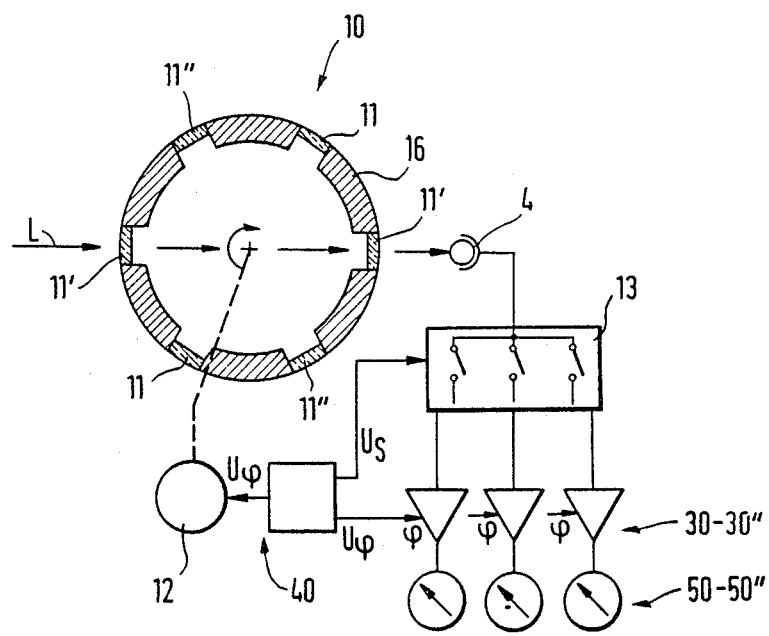
FIG. 4 shows an arrangement for the examination of spectrums in different ranges.

In the arrangement shown in FIG. 4, several filters 11, 11', 11" are held in a common rotary lens housing 16. The filters (or filter pairs) 11, 11' and 11" present differing transmission bands at different times so that, on the one hand, each individual filter (pair) 11, 11', and 11" is displaced in its transmission band as a result of the rotation of the housing 16 and, on the other hand, all the filter pairs 11, 11' and 11" are brought successively into the path of rays between the source 11 and the detector 4. The second filter at any given time can of course also be omitted.

The detector 4 is connected to the input of a multiplexer 13 whose outputs are provided with three lock-in-amplifiers 30, 30' and 30" having separate display elements 50, 50' and 50". The control apparatus 40 also controls the multiplexer 13 in such a way that a corresponding lock-in-amplifier 30, 30' and 30" cooperates with each of the filters 11, 11' and 11". In addition, the phase signal $U_\phi$ is provided by the control apparatus 40 and supplied both to the motor 12 for the filter arrangement 10 and to the lock-in-amplifiers 30, 30' and 30".

Of course, a demultiplexer can be positioned after the lock-in-amplifiers so that only one display apparatus is necessary. Advantageously, however, use is made of a number of channels corresponding to the number of lock-in-amplifiers whose cut-off frequencies, at any given time, should be chosen as low as possible.

Figure 5:
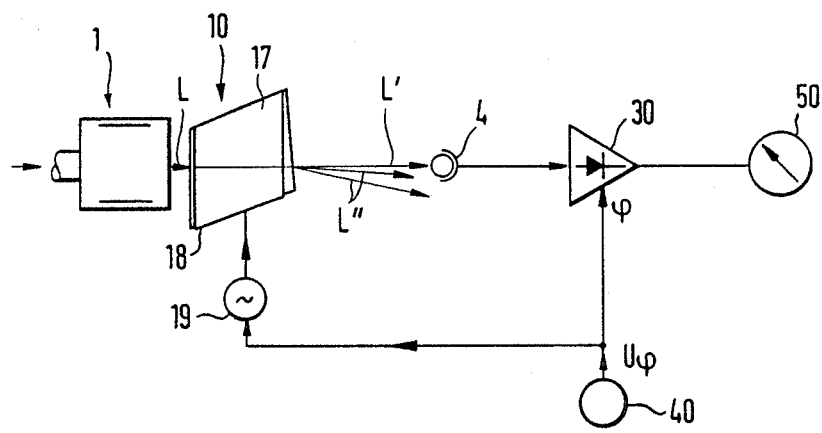
FIG. 5 is an arrangement similar to the arrangement shown in FIG. 1, but having an eletrically selective filter.

A further preferred embodiment of the arrangement according to the invention is shown in FIG. 5. This differs from the arrangement shown in FIG. 1 in that the filter arrangement 10 is an electrically adjustable filter 17. Such filters consist of a $TeO_2$ crystal in which shear waves are induced over an ultrasonic transducer 18 and passed through the crystal. At the same time, because of the Bragg-Effect, a filter effect is achieved whose frequence position (wavelength position) depends on the induced ultrasonic frequency. The emergent ray L' which travels to the detector 4 is therefore a narrow band width section of the incident ray L. The rays L" are not used (different or no filtering). As the frequency condition of the filter arrangement 10 depends on the induced ultrasonic wave, a voltage controlled oscillator (VCO) 19 is inserted between the phase-generator 40 and the ultrasonic transducer 18. Consequently, with this arrangement, the frequency position of the analyzed lightbeam L' is proportional to the output voltage of the phase generator 40.

Test results obtained with an arrangement similar to that shown in FIG. 1 are hereinafter described with reference to FIGS. 6 and 7.

Figure 6:
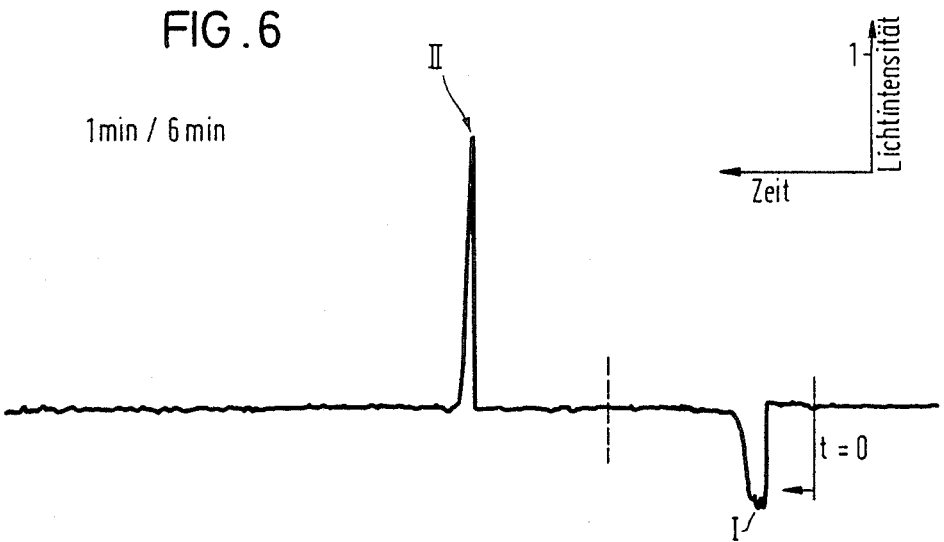
FIGS. 6/7 are spectrogrammes which were recorded with an arrangement according to FIG. 1.
Figure 7:
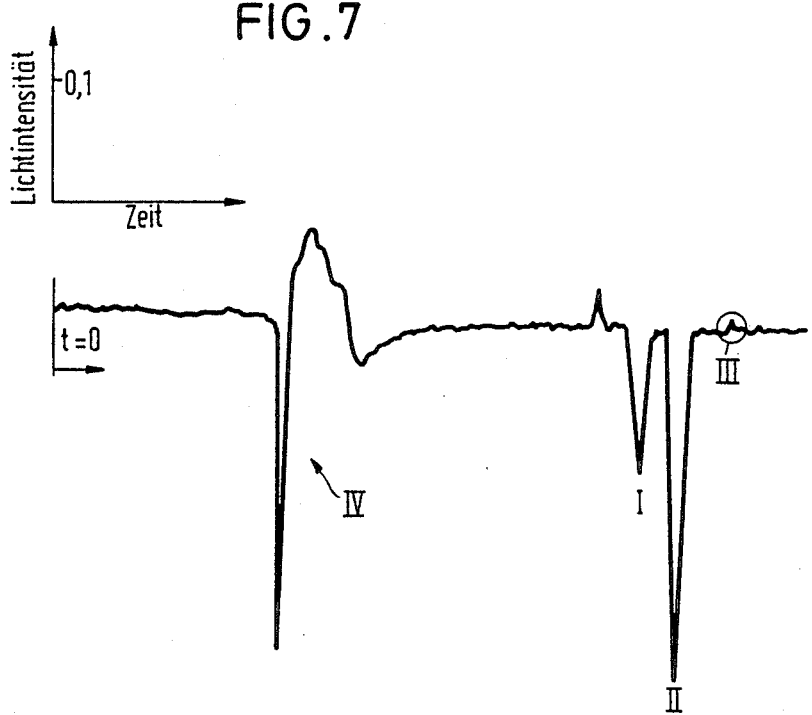

FIG. 6 shows a chromatogram for chlorine (capillary column) in which the filter 11 was an interference filter with a half-width value of about 0.1 nm. The filter was tilted with an oscillation frequency of 7 Hz (higher frequencies yield even better results). The solvent-peak is labelled I, the peak produced with a 40 ng mass of 1,3,5-Trichlorobenzol is labelled II. It is also remarkable that through the process according to the invention or the corresponding apparatus, the actual peak is oppositely directed to the background peak. The broken vertical line in FIG. 6 separates the right hand zone recorded with slower paper feed from the left hand zone recorded with faster paper feed.

A chromatogram for chlorine (capillary column) of only 2 ng chlorine (!) in the form of 1,3,5-Trichlorbenzol is shown (Peak III) and, indeed, in addition to a $10^4$-fold excess in carbon in the form of n-Dekan (Peak I) as well as a $10^4$-fold excess in Bromine in the form of 1,4-Dibromutan (Peak II). Because impurities are registered as negative peaks, there is a selectivity of more than $10^6$, that is to say, absolute specificity. Peak IV concerns a signal which resulted from a short-term discharge of plasma (on the basis of an excess of solvent) and following ignition. Furthermore, it must be noted from the drawing that the light intensity in FIG. 7 was shown with a ten-fold intensification compared with that shown in FIG. 6.

The analytic column can, for example, be loaded as an ion chromatography detector with $Li^+$ ions instead of $H^+$ or $OH^-$ ions and lithium emission of the eluat measured with the process according to the invention. Such a spectroscopic detector is substantially more sensitive than the normally used conductivity selector. Furthermore, the process according to the invention can be used as an HPLC detector, by means of which all elements are recorded substantially more sensitively and more selectively than in the commercially available UV-detectors, so long as they are not present in the eluation medium.

I claim:

1. A method for improving the selectivity of spectrometric measurements of a spectral source to be analyzed, said spectrometric measurements taken over a spectral region of interest, said process comprising the steps of:
    passing an emission said spectral source through a spectral filter, such that said spectral filter transmits a spectral band of said spectral source therethrough;
    transmitting said spectral band from said spectral filter to a detector, said detector generating an output signal in response thereto;
    changing the spectral band transmitted through said spectral filter such that said spectral band is tuned to a phase reference signal;
    transmitting said phase reference signal to a lock-in amplifier, such that the phase reference signal is the lock-in signal of said lock-in amplifier;
    transmitting said detector output signal to said lock-in amplifier, said lock-in amplifier generating an output signal in response thereto;
    monitoring said lock-in amplifier output; and
    periodically varying said phase reference signal across said spectral region of interest.

2. The method of claim 1 wherein said spectrometric measurements are of a light spectrum and said filter is an optical filter and wherein the step of changing the spectral band transmitted through said spectral filter comprises changing the transmission band of said optical filter.

3. The method of claim 1 wherein said spectrometric measurements are of a mass spectrum, utilizing a mass spectrometer, said mass spectrometer having at least one sector magnet and an aperture and wherein said spectral filter comprises a superimposed magnetic field on said mass spectrometer sector magnet and the step of changing the spectral band transmitted through said spectral filter comprises rapidly oscillating said superimposed magnetic field.

4. The method of claim 1 wherein said spectrometric measurements are of a mass spectrum, utilizing a mass spectrometer, said mass spectrometer having at least one sector magnet and an aperture, wherein said spectral filter comprises said mass spectrometer aperture and wherein the step of changing said spectral band transmitted through said spectral filter comprises oscillating said aperture.

5. The method of claim 1 wherein said spectrometric measurements are of a mass spectrum, utilizing a mass spectrometer, wherein the step of changing the spectral band transmitted through said spectral filter comprises the step of producing and oscillating an electrostatic deflection field in said mass spectrometer which oscillates at a rate proportional to the rate at which said reference signal is varied.

6. A spectrometric measurement apparatus for analyzing a source over a pre-determined spectral region of interest, comprising:
    control means for generating a phase reference signal which is periodically varied over the pre-determined region of interest;
    spectral filter means for transmitting a spectral band from the spectral region of said source, said spectral filter means being responsive to said phase reference signal such that the spectral band therethrough is tuned to said reference signal;
    a lock-in amplifier tuned to said reference signal such that the lock-in signal of said lock-in amplifier is said phase reference signal, said lock-in amplifier generating an output signal in response to an amplifier source signal;
    detector means for receiving said spectral band transmitted through said spectral filter and generating an output signal in response thereto, said output signal transmitted to said lock-in amplifier as said amplifier source signal;
    monitoring means for monitoring said output from said lock-in amplifier.

7. The apparatus of claim 6 wherein said spectrometric measurements are of a light spectrum and wherein said filter means comprises optical filter means, wherein the transmission band of said optical filter means is dependent on the angle of incidence of light thereon, and wherein said apparatus further comprises means for changing the angle of said filter means in response to said phase reference signal.

8. The apparatus of claim 7 wherein said means for changing the angle of said optical filter means comprises a rotary drive responsive to said phase reference signal.

9. The apparatus of claim 6 wherein said spectrometric measurements are of a light spectrum and said filter means comprises optical filter means, wherein the transmission band of said optical filter means is dependent on the angle of incidence of light thereon, and wherein said apparatus further includes means for changing the angle of incidence of light on said optical filter means comprising a mirror disposed such that said mirror receives said light spectrum from said source and reflects said light spectrum to said optical filter means; and wherein said apparatus further includes rotating means responsive to said reference signal for changing the angle of said mirror.

10. The apparatus of claims 6, 7 or 8 wherein said filter means comprises a plurality of optical filters, each of said filters having a different optical transmission band; and wherein said apparatus further comprises:

drive means for changing the position of said filter means such that said detector successively probes said filters in said filter means;

a multiplexer responsive to the output of said detector and having an output associated with each of said filters; and a plurality of lock-in amplifiers responsive to the outputs of said multiplexer, wherein said drive means and said multiplexer are responsive to said reference signal such that a lock-in amplifier is associated with and cooperates with a corresponding optical filter.

* * * * *

UNITED STATES PATENT AND TRADEMARK OFFICE
CERTIFICATE OF CORRECTION

PATENT NO. : 4,804,271
DATED : February 14, 1989
INVENTOR(S) : Karl Cammann

It is certified that error appears in the above-identified patent and that said Letters Patent is hereby corrected as shown below:

In column 2, line 14, please delete "greaeer" and substitute therefor --greater--.

In column 3, line 64, after "mirror" please delete the first occurrence of "A".

IN THE CLAIMS

In column 5, line 44, after "emission" please insert --from--.

Signed and Sealed this

Twenty-first Day of May, 1991

Attest:

HARRY F. MANBECK, JR.

*Attesting Officer*      *Commissioner of Patents and Trademarks*